(12) United States Patent
Kim

(10) Patent No.: US 10,639,504 B2
(45) Date of Patent: May 5, 2020

(54) HIGH-INTENSITY FOCUSED ULTRASOUND DEVICE

(71) Applicant: You In Kim, Cheongju-si (KR)

(72) Inventor: You In Kim, Cheongju-si (KR)

( * ) Notice: Subject to any disclaimer, the term of this patent is extended or adjusted under 35 U.S.C. 154(b) by 411 days.

(21) Appl. No.: 15/578,373

(22) PCT Filed: Dec. 18, 2015

(86) PCT No.: PCT/KR2015/013965
§ 371 (c)(1),
(2) Date: Nov. 30, 2017

(87) PCT Pub. No.: WO2017/026597
PCT Pub. Date: Feb. 16, 2017

(65) Prior Publication Data
US 2018/0154185 A1 Jun. 7, 2018

(30) Foreign Application Priority Data
Aug. 13, 2015 (KR) .................. 10-2015-0114327

(51) Int. Cl.
*A61N 7/02* (2006.01)
*A61N 7/00* (2006.01)
*A61N 5/06* (2006.01)
*A61B 18/14* (2006.01)
*A61B 18/00* (2006.01)
(Continued)

(52) U.S. Cl.
CPC ............. *A61N 7/02* (2013.01); *A61N 5/0616* (2013.01); *A61N 7/00* (2013.01); *A61B 18/14* (2013.01); *A61B 2017/00477* (2013.01); *A61B 2018/00005* (2013.01); *A61B 2018/00017* (2013.01); *A61B 2018/00994* (2013.01); *A61B 2034/2063* (2016.02); *A61B 2034/2065* (2016.02); *A61N 2005/005* (2013.01); *A61N 2005/067* (2013.01); *A61N 2005/0644* (2013.01); *A61N 2007/0034* (2013.01); *A61N 2007/0052* (2013.01); *A61N 2007/0069* (2013.01); *A61N 2007/0091* (2013.01); *A61N 2007/027* (2013.01)

(58) Field of Classification Search
None
See application file for complete search history.

(56) References Cited

U.S. PATENT DOCUMENTS

2004/0039312 A1 2/2004 Hillstead et al.
2008/0194965 A1* 8/2008 Sliwa ...................... A61N 7/02
600/459

(Continued)

FOREIGN PATENT DOCUMENTS

JP 2005-517488 A 6/2005
KR 10-2009-0034925 A 4/2009
(Continued)

*Primary Examiner* — Katherine L Fernandez
*Assistant Examiner* — Yi-Shan Yang
(74) *Attorney, Agent, or Firm* — Rabin & Berdo, P.C.

(57) ABSTRACT

A high-intensity focused ultrasound is configured such that a disposable separable cartridge is attached to and detached from the ultrasound device, so that a practitioner, i.e. a doctor, can obtain coordinates of a skin tissue of a subject using a scanner of an ultrasonic transducer and locate an accurate procedure point in real time. A procedure can be performed on the accurate procedure point of the skin tissue without repeated procedures.

6 Claims, 5 Drawing Sheets

(51) Int. Cl.
  *A61B 34/20* (2016.01)
  *A61B 17/00* (2006.01)
  *A61N 5/00* (2006.01)
  *A61N 5/067* (2006.01)

(56) References Cited

U.S. PATENT DOCUMENTS

2010/0042019 A1*  2/2010  Desilets .............. A61B 8/0858
                                                          601/2
2010/0217253 A1    8/2010  Mehta
2011/0072970 A1    3/2011  Slobodzian et al.
2012/0296240 A1*  11/2012  Azhari .................... A61N 7/02
                                                          601/2
2016/0375271 A1*  12/2016  Tsoref ...................... A61N 7/00
                                                          601/2
2017/0214861 A1*   7/2017  Rachlin ................... G03B 5/00

FOREIGN PATENT DOCUMENTS

| KR | 10-2012-0090007 A |   | 8/2012 |
| KR | 10-2012-0101640 A |   | 9/2012 |
| KR | 10-2012-0128276 A |   | 11/2012 |
| KR | 1020120128276 A | * | 11/2012 |
| KR | 10-1574951 B1 |   | 12/2015 |

* cited by examiner

HIGH-INTENSITY FOCUSED ULTRASOUND DEVICE

TECHNICAL FIELD

The present invention relates to a high-intensity focused ultrasound device. More particularly, the present invention relates to a high-intensity focused ultrasound device, a structure of which is designed such that a disposable separable cartridge is attached to and detached from the ultrasound device, such that a practitioner, i.e. a doctor, can obtain coordinates of a skin tissue of a subject using a scanner of an ultrasonic transducer and locate an accurate procedure point in real time, thereby allowing a procedure to be performed on the accurate procedure point of the skin tissue without repeated procedures.

BACKGROUND ART

Generally, a high intensity focused ultrasonic surgical unit (HIFU) performs a treatment using heat energy generated at a focus point (focal point) by irradiating ultrasound into the tissue using a transducer. Until now, the HIFU has been used mainly in treating liver cancer, breast cancer, uterine cancer, and the like. Such a principle is also applied to skin care, i.e. the skin is reshaped as a whole by strongly transferring focused ultrasound energy to the lower dermis, the boundary layer between dermis and subcutaneous fat, the superficial muscular aponeurotic system (SMAS) of fibrous tissues of fat layers, fasciae, and so on.

Generally, it is known that a single procedure results in a face lifting effect and a tightening effect, with collagen and elastin being continuously generated for 3 to 6 months.

However, since a high-intensity focused ultrasound generation device can operate over a limited period of time, medical fees, borne by medical consumers who want beauty therapy, are increased, which is problematic.

In addition, a portion of the skin can be lifted by transferring ultrasound energy to a depth of 3 mm to 4.5 mm (SMAS layer) from the skin surface, but it is difficult to regenerate a large amount of collagen at the same time, thereby causing rapid curing to be difficult.

However, since the service life of a separable cartridge is limited according to the intensity of output ultrasound generated by the ultrasound operation device, the ultrasound operation device requires periodic replacing of the separable cartridge.

In this case, due to high-intensity focused ultrasound output, high-temperature heat is generated by a transducer and a cartridge printed circuit board (PCB) of the separable cartridge, a main PCB of a probe body, and a like. This may reduce a service life to be shorter than an original life time. Thus, a consumption article, i.e. a hand piece, may be frequently replaced, thereby imposing a heavy cost burden on a user. It is therefore necessary to introduce a cooling means capable of increasing the service life of a cartridge by effectively lowering heat generated in a body.

In addition, although such a cooling means has been introduced, an accurate procedure point cannot be located in real time, leading to a danger of skin damage or a thermal burn.

DISCLOSURE

Technical Problem

Accordingly, the present invention has been made keeping in mind the above problems occurring in the prior art, and an object of the present invention is to provide a high-intensity focused ultrasound device able to minimize external injuries and pain by transferring ultrasound heat to a target layer, i.e. a superficial muscular aponeurotic system (SMAS) layer, by continuously forming stitches as in sewing using a hand piece body including a separable cartridge, lift a portion of the skin by transferring focused ultrasound energy to the SMAS layer from a skin surface while generating collagen at the same time using a laser beam, and additionally use radio frequency (RF) waves.

Another object of the present invention is to provide a high-intensity focused ultrasound device allowing a practitioner, i.e. a doctor, to obtain coordinates of a skin tissue of a subject via a scanner of an ultrasonic transducer. The high-intensity focused ultrasound device can accurately set coordinates of a procedure point of the skin tissue such that the accurate procedure point can be located in real time, thereby performing a procedure only on the accurate procedure point without repeated procedures.

Technical Solution

In order to accomplish the above object, the present invention provides a high-intensity focused ultrasound device including a hand piece including a hand piece body electrically connected to a freely movable body through a wire and a separable cartridge disposably coupled to the hand piece body. The hand piece body includes: a laser beam generator fractionally transferring energy to facilitate synthesis of collagen; an ultrasonic transducer receiving electrical energy impedance-matched through a frequency generation process and a power amplification process to convert the received electrical energy into high-intensity focused ultrasound and irradiate the high-intensity focused ultrasound or receiving the reflected ultrasound; an X-Y reflecting mirror undergoing a forward/backward movement and a tilting movement inside the hand piece body to sequentially form HIFU foci in a single row, in a plurality of rows, or in a circular row; a cooling device supplying a cooling gas to the separable cartridge; and a zoom-in device zooming in an image generated by reflected ultrasound. The separable cartridge includes: a cooling passage injecting a cooling gas, allowing the cooling gas to flow through a bottom surface of the separable cartridge, and lowering temperature; and a transparent transmittance member supporting the cooling passage and coming into close contact with a skin tissue such that a laser beam and high-intensity focused ultrasound contact a portion of skin. The movable body includes: a controller including an ultrasonic transducer-module controlling a frequency generation process and a power amplification process of the ultrasonic transducer, and power, a frequency, a duty cycle, a focus size, and a pulse repetition frequency, a reflecting mirror control module controlling the forward/backward movement and the tilting movement according to an X-axis and an Y-axis of the X-Y reflecting mirror, a cooling module lowering a temperature of the cooling device when a retreatment is performed, a coordinate module receiving information on converted coordinates through the ultrasonic transducer and locating a site currently treated, and a zoom-in module performing control to zoom in to the image generated by the reflected ultrasound; a monitor unit including an indicator indicating information related to a procedure of a practitioner and a touch screen through which the practitioner operates or controls the high-intensity focused ultrasound generation device; and a power supply supplying high-intensity focused ultrasound power.

The controller may further include: a scanner locating a shape and a treatment position of the site currently treated, by receiving reflected ultrasound through the ultrasonic transducer; and a cooling device driving unit lowering the temperature of the cooling device when a retreatment is performed on the site currently treated.

The hand piece body may further include a coordinate sensor. The coordinate sensor calculates coordinates of the HIFU foci concentrated in the single row, in the plurality of rows, or in the circular row to pass through the transparent transmittance member, and increases an amount of the cooling gas supplied to prevent a burn hazard when coordinates of newly concentrated HIFU foci match the calculated coordinates of the HIFU foci.

The hand piece body further includes a temperature sensor, and the controller receives a temperature measured by the temperature sensor in real time, determines in real time whether a temperature of the cooling gas is within an appropriate operation temperature range, and controls the temperature of the cooling device.

The transparent transmittance member may include a pair of ultrasound windows transmitting ultrasound disposed with respect to a laser beam window transmitting a laser beam or two pairs of ultrasound windows disposed in a cross shape with respect to the laser window.

Advantageous Effects

As described above, according to the present invention, the structure of the high-intensity focused ultrasound device is designed such that a disposable separable cartridge can be attached to and detached from the ultrasound device even when the hand piece body is deformed or broken due to high-temperature heat generated by high-intensity focused ultrasound output. This can consequently increase the service life of the high-intensity focused ultrasound device while reducing maintenance costs of the high-intensity focused ultrasound device, such that medical fees, borne by medical consumers who want beauty therapy, can be reduced to a reasonable level.

In addition, according to the present invention, it is possible to minimize external injuries and pain in such a manner that stitches are continuously formed as in sewing and lift a portion of the skin by transferring focused ultrasound energy to a depth of 3 mm to 4.5 mm (SMAS layer) from a skin surface while regenerating collagen at the same time, so that skin lifting can be effectively performed without an incision.

Furthermore, according to the present invention, a large amount of collagen can be regenerated by using a laser beam at the same time, so that lifting can be effectively performed without an incision during skin therapy and a healing time can be reduced.

In addition, according to the present invention, the high-intensity focused ultrasound device can be disposed more adjacently to skin, due to a skin contact cartridge structure having a cooling passage disposed in a portion to be brought into close contact with a portion of the skin, thereby preventing skin burns.

Furthermore, according to the present invention, another scheme for preventing skin burns in a procedure allows a practitioner, i.e. a doctor, to obtain coordinates of a skin tissue of a subject using the scanner of the ultrasonic transducer. Coordinates of a procedure point of the skin tissue can be accurately set such that the monitors can locate the accurate procedure point in real time using a zoom-in function, thereby performing a procedure on the accurate procedure point without repeated procedures.

In addition, according to the present invention, it is possible to calculate coordinates of high intensity focused ultrasonic surgical unit (HIFU) foci concentrated in a single row, in a plurality of rows, or in a circular row and to determine whether or not coordinates of newly concentrated HIFU foci match the calculated coordinates of the HIFU foci, thereby performing a procedure on an accurate site without repeated procedures and preventing skin burns. The entirety of information on skin coordinates of a subject can be stored and reused, such that skin therapy procedures can be systematically managed.

BEST MODE

Mode for Invention

Figure 1:
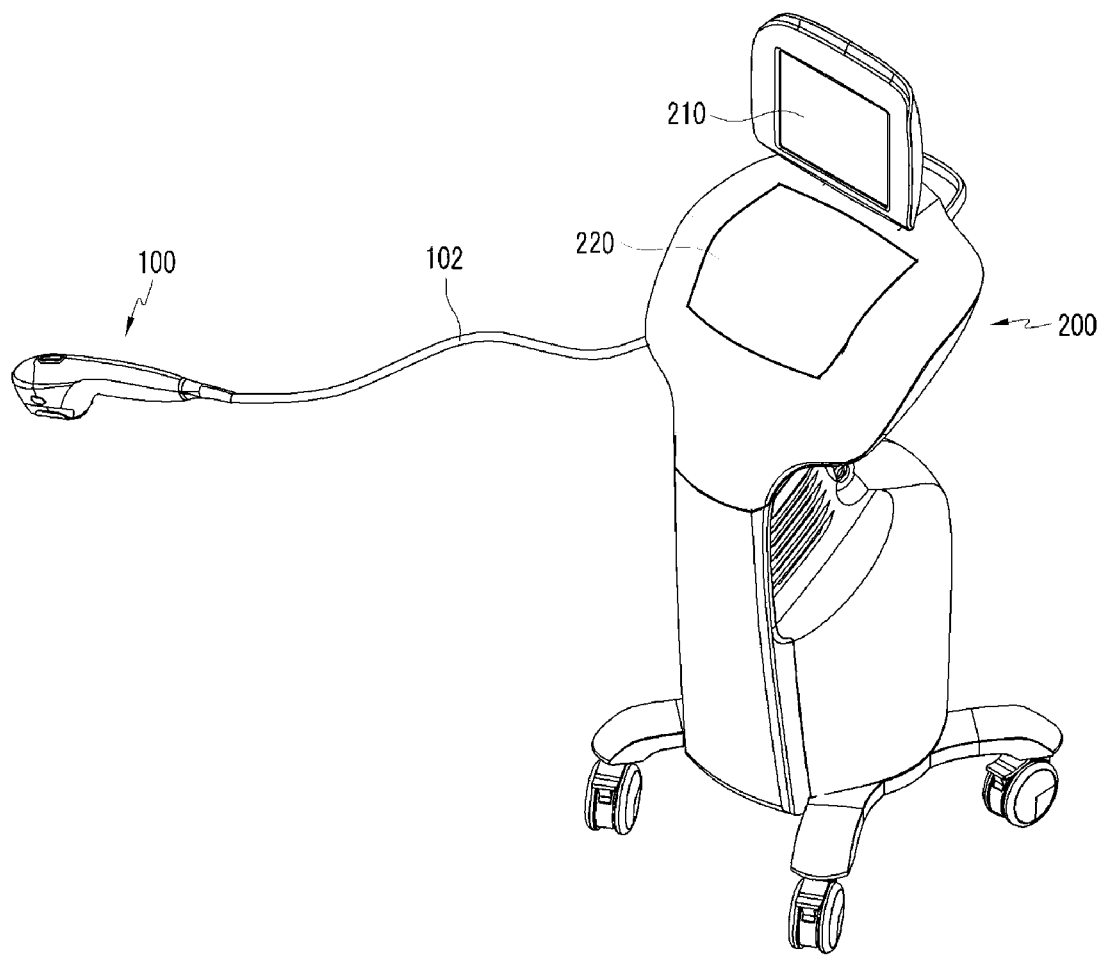
FIG. 1 is a block diagram illustrating an overall configuration of a high-intensity focused ultrasound device according to the present invention.

In order to fully understand the present invention, exemplary embodiments of the invention will be described with reference to the accompanying drawings. The embodiments of the present invention may be modified in many different forms and the scope of the invention should not be limited to the embodiments set forth herein. Rather, these embodiments are provided so that this disclosure will be thorough and complete, and will fully convey the concept of the invention to those skilled in the art. In the drawings, the shapes and dimensions may be exaggerated for clarity, and the same reference numerals will be used throughout to designate the same or like components. Detailed explanations of known related functions and constitutions may be omitted to avoid unnecessarily obscuring the subject matter of the present invention.

Figure 2:
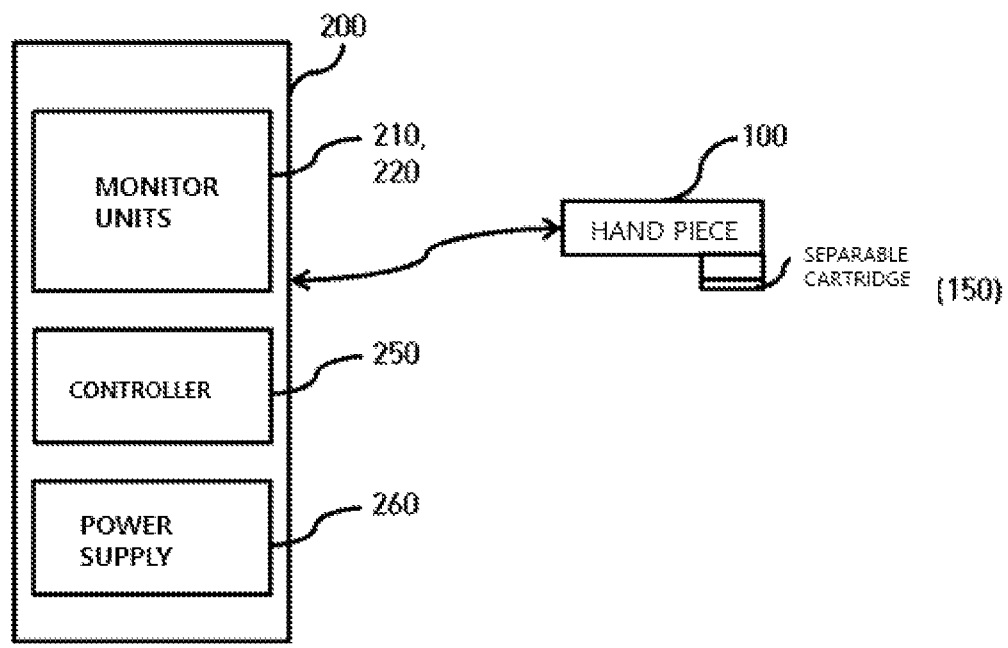
FIG. 2 is a block diagram illustrating the high-intensity focused ultrasound device of FIG. 1.

As illustrated in FIGS. 1 and 2, a hand piece according to the present invention includes a hand piece body 100 electrically connected to a movable body 200 through a wire 102 and a separable cartridge 150 disposably coupled to the hand piece body 100, the movable body 200 having a large touch screen monitor 220 on a front portion thereof. When high temperature is caused by heat generated due to high-intensity focused ultrasound output or a lifespan of the separable cartridge 150 is ended, the separable cartridge 150 can be simply replaced. Accordingly, the present invention is economical.

Figure 3:
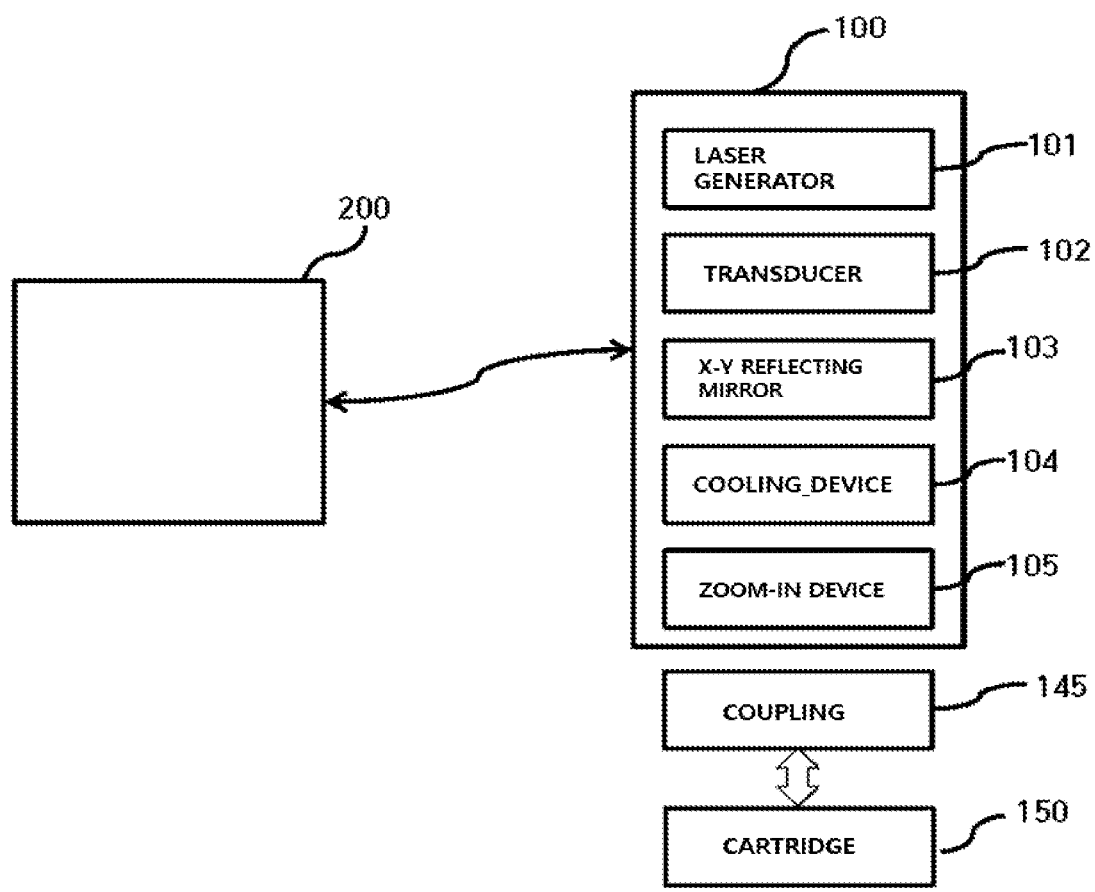
FIG. 3 is a block diagram illustrating a hand piece of FIG. 2.

As illustrated in FIG. 3, the hand pieces body 100 according to the present invention includes a laser beam generator 101, an ultrasonic transducer 102, an X-Y reflecting mirror 103, a cooling device 104, and a zoom-in device 105. The movable body 200 includes a controller 250, monitor units 210 and 220, and a power supply 260. The separable cartridge 150 includes a transparent transmittance member 151 to transmit light generated by the laser generator 101 and the ultrasonic transducer 102.

In an example, the separable cartridge 150 includes the transparent transmittance member 151 and a cooling hose 110. The separable cartridge 150 may be coupled to the hand piece body 100 in such a manner that a mechanical coupling 145 formed at a portion of the hand piece body 100 and a mechanical coupling shape formed at a portion of the separable cartridge 150 so as to correspond to the mechanical coupling 145 are engaged with each other through mechanical coupling (coupling between a male shape and a female shape).

In addition, a case of the separable cartridge 150 is generally formed from a thermal conductive plastic resin. It is desirable that the transparent transmittance member 151 is disposed on a lower surface of the case and is formed from a material having excellent heat conductivity such that cooling of a cooling gas is not externally discharged from a cooling passage 155. That is, the transparent transmittance member 151 may be formed from an alloy of various transparent metals having heat conductivity greater than that of the case.

The laser generator 101 is a laser beam generating device that fractionally transfers energy to facilitate synthesis of collagen.

The ultrasonic transducer 102 is an ultrasound receiving device that receives electrical energy impedance-matched through a frequency generation process and a power amplification process to convert the electrical energy into high-intensity focused ultrasound and irradiate the high-intensity focused ultrasound, or receives reflected ultrasound.

In addition, the ultrasonic transducer 102 has a concave shape in which ultrasound is generated, and a central point at which a focusing point of ultrasound is formed.

Figure 4:
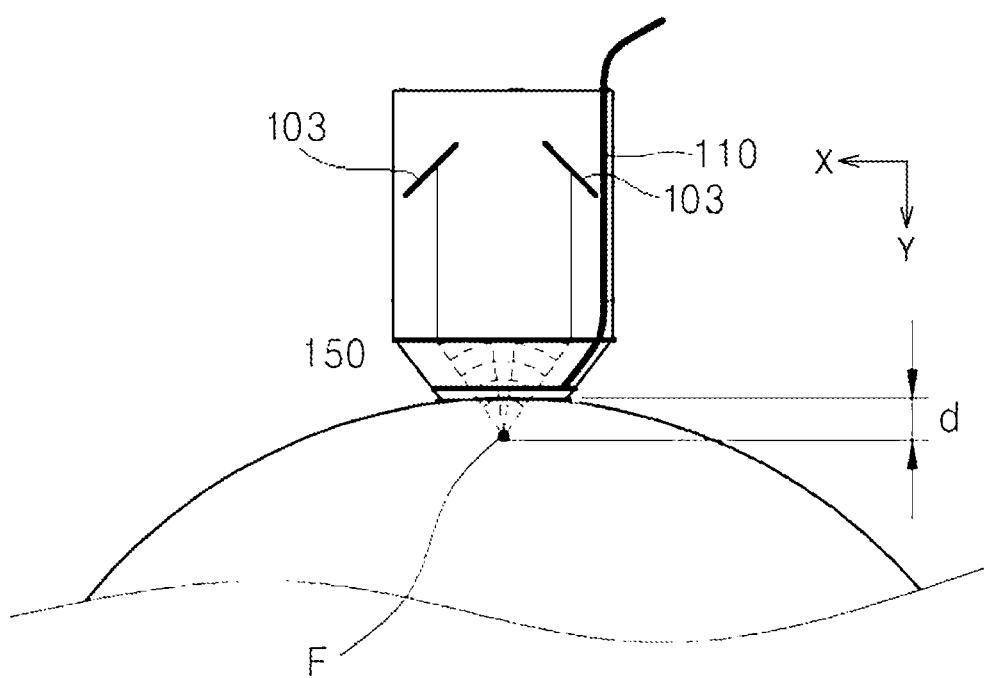
FIG. 4 is a diagram illustrating an operation method of an X-Y reflecting mirror according to an embodiment of the present invention.

As illustrated in FIGS. 3 and 4, the X-Y reflecting mirror 103 concurrently undergoes a forward/backward movement and a tilting movement inside the hand piece body to sequentially form HIFU foci in a single row, in a plurality of rows, or in a circular row to reach a depth of 3 mm to 4.5 mm (d: SMAS layer) of a skin surface through the transparent transmittance member 151 of the separable cartridge 150.

Therefore, according to the present invention, external injuries and pain can be minimized in such a manner that stitches are continuously generated as in sewing, and a portion of the skin can be lifted and collagen can be regenerated at the same time using a laser beam by transferring focused ultrasound energy to a depth of 3 mm to 4.5 mm (superficial muscular aponeurotic system (SMAS) layer) from a skin surface.

The X-Y reflecting mirrors 103 of FIG. 3 may disperse a laser beam and ultrasound in a line shape and may sequentially move to irradiate the laser and the ultrasound and inject energy in a plane shape, thereby maximizing a lifting effect. In another example, one of the X-Y refection mirrors may be a mirror for laser reflection and the other may be a mirror for ultrasound reflection.

When the zoom-in device 105 of FIG. 3 zooms in an image of a skin tissue of a subject, captured through a scanner by a practitioner, i.e. a doctor, using a zoom-in function, an accurate procedure point can be clearly viewed, thereby performing a smoother procedure.

Figure 5:
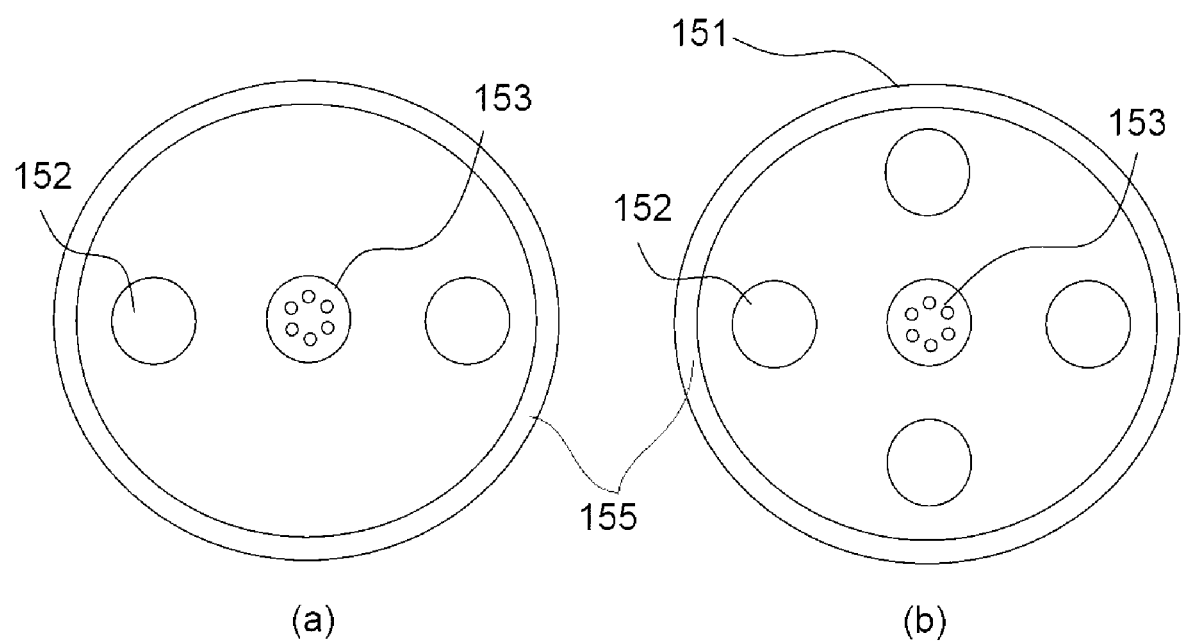
FIG. 5 is a plan view illustrating a transparent transmittance member of a separable cartridge according to an embodiment of the present invention.

As illustrated in FIG. 5, the cooling device 104 is a device that supplies a cooling gas to the cooling passage 155 having a column shape of the separable cartridge 150 using the cooling hose 110, and allows the cooling gas to flow through a bottom surface of the separable cartridge, thereby cooling a corresponding portion of the skin. Although not illustrated in detail in drawings, in order for the cooling gas to pass through a surface of the transparent transmittance member 151, an inlet port is formed in one end of the cooling passage 155 and an outlet port is formed in the other end of the cooling passage 155.

The transparent transmittance member 151 is a film that supports the cooling passage 155 and coming into close contact with a skin tissue such that the laser and the high-intensity focused ultrasound contact a portion of the skin. The transparent transmittance member 151 may have a front surface, i.e. an inner peripheral surface having a parabolic shape to focus a wavelength.

In an example, as illustrated in (a) of FIG. 5, a pair of ultrasound windows 152 are disposed with respect to a laser beam window 153, and as illustrated in (b) of FIG. 5, two pairs of ultrasound windows 152 are disposed in a cross shape with respect to the laser window 153. Accordingly, a procedure may be easily performed on a site on which the HIFU foci are concentrated in a single row, in a plurality of rows, or in a circular row.

In an embodiment of the present invention, the controller 250 includes an ultrasonic transducer-module, a reflecting mirror control module, a cooling module, and a coordinate module.

In an example, the controller 250 may use the modules to perform lifting in which skin tissues of a dermis layer and an SMAS layer are immediately coagulated to lift a portion of the skin. In order to perform a procedure by concentrating high strength focused ultrasound to a focus through the X-Y reflecting mirror 103 and maintaining energy intensity to be equal to or less a certain J value, the controller 250 may control the frequency generation process and the power amplification process, power, a frequency, a duty cycle, a focus size, and a pulse repetition frequency of the ultrasonic transducer, the forward/backward movement and the tilting movement according to the X-axis and the Y-axis of the X-Y reflecting mirror 103, and a temperature of the cooling device.

The controller 250 receives information on converted coordinates through the ultrasonic transducer and locates a site currently treated, and lowers the temperature of the cooling device when a retreatment is performed.

In addition, the movable body 200 includes the monitor units 210 and 220 including an indicator indicating information related to a procedure of a practitioner and a touch screen through which the practitioner operates or controls the high-intensity focused ultrasound generation device; and the power supply 260 supplying high-intensity focused ultrasound power. The hand piece body 100 according to the present invention may further include a coordinate sensor (not illustrated). The coordinate sensor may calculate coordinates of the HIFU foci concentrated in a single row, in a plurality of rows, or in a circular row to pass through the transparent transmittance member. When coordinates of newly concentrated HIFU foci match the calculated coordinates of HIFU foci, the amount of the cooling gas supplied can be increased to prevent a burn hazard.

That is, the coordinate sensor may set coordinates of a shape and a treatment position of a treatment site received through the scanner in the hand piece body.

The controller 250 may further include the scanner determining a shape and a treatment position of a site currently treated, by receiving ultrasound reflected through the ultrasonic transducer and a cooling device driving unit lowering the temperature of the cooling device when a retreatment is performed on the site currently treated.

In addition, according to the present invention, the practitioner, i.e. the doctor, can obtain coordinates of a skin tissue of a subject through the scanner of the ultrasonic transducer. Coordinates of an accurate procedure point of the skin tissue can be set such that the monitors 210 and 220 locate the accurate procedure point in real time using a zoom-in function under control of the zoom-in module of the controller, thereby performing a procedure on the accurate procedure point without repeated procedures.

In an example, since information on coordinates of a whole skin, transmitted through the scanner, is stored and reused, even after many years, it can be determined whether coordinates of newly concentrated HIFU foci match coordinates of HIFU foci concentrated in a single row, in a plurality of rows, or in a circular row, related to a site on which a procedure is previously performed site, thereby systematically managing a procedure of the whole skin.

According to the configuration of the present invention described above, precise coagulation inside a skin tissue can be induced by ultrasound, thereby improving stability of a dermatological procedure for unwrinkling.

In addition, a temperature value measured by a temperature sensor added according to an embodiment of the present invention is transmitted to the controller 250 in real time. The controller 250 determines in real time whether the temperature of the cooling gas is within an appropriate operation temperature range. In an example, the temperature sensor may be installed in the separable cartridge.

An RF plate (not illustrated) may be further added to the separable cartridge to generate a radio frequency (RF) wave and burns fat.

When an RF wave is applied to the RF plate added according to an embodiment of the present invention, among ions of cell molecules constituting a skin tissue, a polarization phenomenon, in which positive charges (cations) are attracted to a negative electrode and negative ions (anions) are attracted to a positive electrode by an RF alternating current, occurs. At this time, Joule's eat is generated in the skin tissue.

According to the configuration of the present invention described above, the structure of the high-intensity focused ultrasound device is designed such that the disposable separable cartridge 150 including the cooling passage 155 can be attached to and detached from the ultrasound device even when the hand piece body 100 is deformed broken due to high-temperature heat generated by high-intensity focused ultrasound output. This can consequently increase the service life of the high-intensity focused ultrasound device while reducing maintenance costs of the high-intensity focused ultrasound device, such that medical fees, borne by medical consumers who want beauty therapy, can be reduced to a reasonable level.

In addition, according to the present invention, it is possible to minimize external injuries and pain in such a manner that stitches are continuously formed as in sewing and lift a portion of the skin by transferring focused ultrasound energy to a depth of 3 mm to 4.5 mm (SMAS layer) from a skin surface while easily regenerating collagen at the same time. Accordingly, unlike an existing procedure, skin lifting can be effectively performed without an incision.

Furthermore, according to the present invention, a large amount of collagen can be regenerated by using a laser beam generated by the laser generator 101, so that lifting can be effectively performed without an incision during skin therapy and a healing time can be reduced.

In addition, according to the present invention, due to the skin contact cartridge structure in which the cooling passage 155 of the separable cartridge 150, to which the cooling gas is supplied using the cooling hose 110, is disposed at a portion to be brought into close contact with a portion of the skin, the high-intensity focused ultrasound device can be disposed more adjacently to the skin, thereby preventing skin burns.

Furthermore, according to the present invention, a practitioner, i.e. a doctor, can obtain coordinates of a skin tissue of a subject using the scanner of the ultrasonic transducer. Coordinates of a procedure point of a skin tissue can be accurately set such that the monitors can locate the accurate procedure point in real time using a zoom-in function, thereby performing a procedure on the accurate procedure point without repeated procedures.

In addition, according to the present invention, it is possible to calculate coordinates of HIFU foci concentrated in a single row, in a plurality of rows, or in a circular row and to determine whether or not coordinates of newly concentrated HIFU foci match the coordinates of the calculated HIFU foci, thereby accurately performing a procedure on a site without repeating and thus preventing skin burns. The entirety of information on skin coordinates of a subject can be stored and reused using the scanner, such that skin therapy procedures can be systematically managed.

What is claimed is:

1. A high-intensity focused ultrasound (HIFU) device comprising a hand piece comprising a hand piece body electrically connected to a freely movable body through a wire and a separable cartridge disposably coupled to the hand piece body,
    wherein the hand piece body comprises:
        a laser beam generator fractionally transferring energy to facilitate synthesis of collagen;
        an ultrasonic transducer receiving electrical energy impedance-matched through a frequency generation process and a power amplification process to convert the received electrical energy into HIFU and irradiate the HIFU, and receiving reflected ultrasound;
        an X-Y reflecting mirror undergoing a forward movement, a backward movement, and a tilting movement inside the hand piece body to sequentially form HIFU foci in a single row, in a plurality of rows, or in a circular row;
        a cooling device supplying a cooling gas to the separable cartridge; and
        a zoom-in device zooming in to an image generated by the reflected ultrasound,
    wherein the separable cartridge comprises:
        a cooling passage injecting the cooling gas, allowing the cooling gas to flow through a bottom surface of the separable cartridge, and lowering temperature; and
        a transparent transmittance member supporting the cooling passage and is adapted to come into contact with a skin tissue such that a laser beam and the high-intensity focused ultrasound contact a portion of the skin tissue, and
    wherein the freely movable body comprises:
        a controller configured to
            control the frequency generation process and the power amplification process of the ultrasonic transducer, power, a frequency, a duty cycle, a focus size, and a pulse repetition frequency;
            control the forward movement, the backward movement and the tilting movement in reference to an X-axis and a Y-axis of the X-Y reflecting mirror, lower a temperature of the cooling device when a retreatment is performed;

receive information on converted coordinates through the ultrasonic transducer and locating a site currently treated; and control a zoom-in function to zoom in to the image generated by the reflected ultrasound;

a monitor unit comprising an indicator indicating information related to a procedure of a practitioner and a touch screen through which the practitioner operates or controls the HIFU device; and a power supply supplying HIFU power.

2. The HIFU device of claim 1, wherein the controller further comprises:

a scanner locating a shape and a treatment position of the site currently treated, by receiving the reflected ultrasound through the ultrasonic transducer, wherein the controller lowers the temperature of the cooling device when the retreatment is performed on the site currently treated.

3. The HIFU device of claim 1, wherein the hand piece body further comprises a coordinate sensor, wherein the coordinate sensor calculates coordinates of the HIFU foci in the single row, in the plurality of rows, or in the circular row, and increases an amount of the cooling gas supplied to prevent a burn hazard when coordinates of newly formed HIFU foci match the calculated coordinates of the HIFU foci.

4. The HIFU device of claim 1, wherein the hand piece body further comprises a temperature sensor, and the controller receives a temperature measured by the temperature sensor in real time, determines in real time whether a temperature of the cooling gas is within an operation temperature range, and controls the temperature of the cooling device.

5. The HIFU device of claim 1, wherein the transparent transmittance member comprises a laser beam window transmitting the laser beam disposed in between a pair of ultrasound windows transmitting ultrasound disposed or two pairs of ultrasound windows disposed in a cross shape with respect to the laser beam window.

6. The HIFU device of claim 2, wherein the hand piece body further comprises a coordinate sensor, wherein the coordinate sensor calculates coordinates of the HIFU foci in the single row, in the plurality of rows, or in the circular row, and increases an amount of the cooling gas supplied to prevent a burn hazard when coordinates of newly formed HIFU foci match the calculated coordinates of the HIFU foci.

* * * * *